(12) United States Patent
Baird

(10) Patent No.: US 9,861,468 B2
(45) Date of Patent: Jan. 9, 2018

(54) TENODESIS IMPLANT AND INSERTER AND METHODS FOR USING SAME

(71) Applicant: Cayenne Medical, Inc., Scottsdale, AZ (US)

(72) Inventor: Kevin N. Baird, Phoenix, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 0 days.

(21) Appl. No.: 15/050,402

(22) Filed: Feb. 22, 2016

(65) Prior Publication Data

US 2016/0242897 A1 Aug. 25, 2016

Related U.S. Application Data

(62) Division of application No. 13/968,272, filed on Aug. 15, 2013, now Pat. No. 9,289,283, which is a division
(Continued)

(51) Int. Cl.
*A61F 2/08* (2006.01)

(52) U.S. Cl.
CPC .......... *A61F 2/0811* (2013.01); *A61F 2/0805* (2013.01); *A61F 2002/0829* (2013.01);
(Continued)

(58) Field of Classification Search
CPC .................................... A61F 2/28; A61F 2/08
(Continued)

(56) References Cited

U.S. PATENT DOCUMENTS

| 5,324,308 A | 6/1994 | Pierce |
| 5,632,748 A | 5/1997 | Beck, Jr. et al. |

(Continued)

FOREIGN PATENT DOCUMENTS

| WO | 9511631 A1 | 5/1995 |
| WO | WO-9511631 A1 | 5/1995 |

OTHER PUBLICATIONS

International Search Report and Written Opinion, dated Oct. 25, 2012, corresponding PCT App. No. PCT/US2012/027551.
(Continued)

*Primary Examiner* — Yashita Sharma
(74) *Attorney, Agent, or Firm* — Schwegman Lundberg & Woessner, P.A.

(57) ABSTRACT

The present invention provides a novel split barbed fixation device for tenodesis, soft tissue reattachment of tendons and ligaments to bones. The insertion device is adapted for an entirely arthroscopic approach while achieving fixation strength with ultimate pullout resistance comparable to interference screws. The device includes an integrated tendon grasper that provides for easy manipulation of the tendon arthroscopically while eliminating the need for external whip stitching of the tendon, thereby reducing preparation time. The device further includes elements that prevent the fixation implant from being destabilized or rotating during deployment and manipulation, including: a depth limiting sheath, a first implant retainer, a first implant retaining step, a tendon grasping needle tube, and an implant keyway for mating the implant to the tube. The implant itself comprises two separate portions mating along a diagonal and having barbed surface features in opposite directions, only one of which contacts the tendon.

17 Claims, 9 Drawing Sheets

Related U.S. Application Data of application No. 13/411,216, filed on Mar. 2, 2012, now Pat. No. 8,512,405.

(60) Provisional application No. 61/449,279, filed on Mar. 4, 2011.

(52) U.S. Cl.
CPC .............. *A61F 2002/0858* (2013.01); *A61F 2002/0888* (2013.01); *A61F 2220/0016* (2013.01); *A61F 2220/0033* (2013.01)

(58) Field of Classification Search
USPC ...... 623/13.11–13.2; 606/151, 232, 300–329
See application file for complete search history.

(56) References Cited

U.S. PATENT DOCUMENTS

| | | | |
|---|---|---|---|
| 5,674,224 | A | 10/1997 | Howell et al. |
| 6,379,361 | B1 | 4/2002 | Beck, Jr. et al. |
| 6,506,190 | B1 | 1/2003 | Walshe |
| 6,562,044 | B1 | 5/2003 | Cooper |
| 6,736,847 | B2 | 5/2004 | Seyr et al. |
| 7,572,283 | B1 | 8/2009 | Meridew |
| 8,512,405 | B2 | 8/2013 | Baird |
| 9,289,283 | B2 | 3/2016 | Baird |
| 2002/0065528 | A1 | 5/2002 | Clark et al. |
| 2009/0287259 | A1 | 11/2009 | Trenhaile et al. |
| 2010/0004683 | A1 | 1/2010 | Hoof et al. |
| 2010/0069958 | A1 | 3/2010 | Sullivan et al. |
| 2010/0174369 | A1 | 7/2010 | Wang et al. |
| 2011/0004258 | A1 | 1/2011 | Stone et al. |
| 2012/0226355 | A1 | 9/2012 | Baird |

OTHER PUBLICATIONS

Office Action, dated Feb. 18, 2014, corresponding Japanese Patent App. No. 2013556652.

Examination Report, dated Aug. 12, 2014, corresponding EP App. No. 12755160.4.

"U.S. Appl. No. 13/411,216, Notice Allowance dated Apr. 29, 2013", 12 pgs.

"U.S. Appl. No. 13/411,216, Notice Allowance dated Jun. 19, 2013", 4 pgs.

"U.S. Appl. No. 13/411,216, Preliminary Amendment dated Nov. 20, 2012", 6 pgs.

"U.S. Appl. No. 13/968,272, Non Final Office Action dated Feb. 26, 2015", 8 pgs.

"U.S. Appl. No. 13/968,272, Notice of Allowance dated Nov. 16, 2015", 10 pgs.

"U.S. Appl. No. 13/968,272, Response dated Jan. 16, 2015 to Restriction Requirement dated Sep. 16, 2014", 3 pgs.

"U.S. Appl. No. 13/968,272, Response dated Feb. 27, 2015 to Non Final Office Action dated Feb. 26, 2015", 5 pgs.

"U.S. Appl. No. 13/968,272, Restriction Requirement dated Sep. 16, 2014", 7 pgs.

"Australian Application Serial No. 2012225762, First Examiners Report dated Jun. 21, 2013", 4 pgs.

"Australian Application Serial No. 2012225762, Response dated Mar. 7, 2014 to First Examiners Report dated Jun. 21, 2013", 21 pgs.

"International Application Serial No. PCT/US2012/027551, International Preliminary Report on Patentability dated Sep. 19, 2013", 6 pgs.

"International Application Serial No. PCT/US2012/027551, International Search Report dated Oct. 25, 2012", 4 pgs.

"International Application Serial No. PCT/US2012/027551, Written Opinion dated Oct. 25, 2012", 4 pgs.

"Japanese Application Serial No. 2013556652, Office Action dated Feb. 18, 2014", 4 pgs.

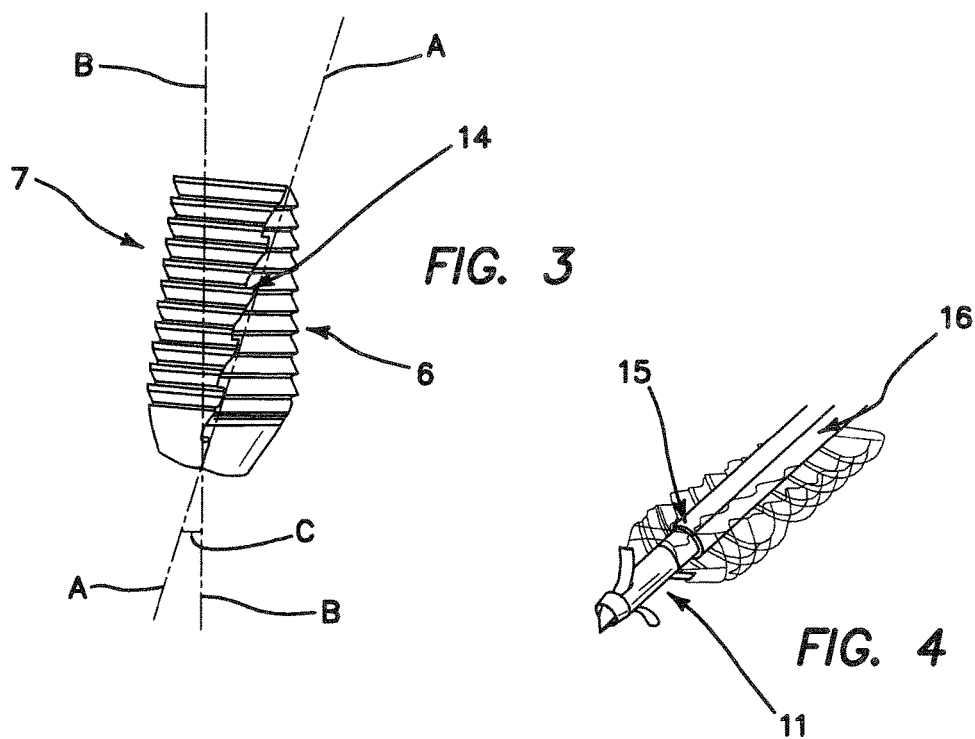
FIG. 3
FIG. 4
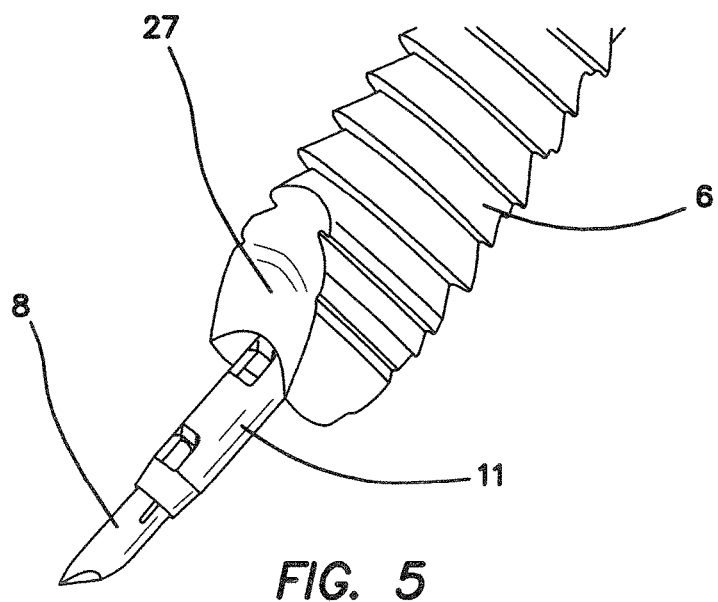
FIG. 5

TENODESIS IMPLANT AND INSERTER AND METHODS FOR USING SAME

This application is a divisional application under 35 U.S.C. 120 of commonly assigned U.S. patent application Ser. No. 13/968,272, entitled Tenodesis Implant and Inserter and Methods for Using Same, filed Aug. 15, 2013 and now allowed, which in turn is a divisional application under 35 U.S.C. 120 of commonly assigned U.S. patent application Ser. No. 13/411,216, entitled Tenodesis Implant and Inserter and Methods for Using Same, filed Mar. 2, 2012 and now U.S. Pat. No. 8,512,405, which in turn claims the benefit under 35 U.S.C. 119(e) of the filing date of Provisional U.S. Application Ser. No. 61/449,279, entitled Tenodesis Implant and Inserter, filed on Mar. 4, 2011. Both prior applications are expressly incorporated herein by reference, in their entirety.

BACKGROUND OF THE INVENTION

The present invention relates to medical devices for securing tendons and ligaments to bones in order to stabilize a joint. More specifically, the present invention is focused on an entirely arthroscopic approach and the benefits that provides (reduced procedure time, recovery time, invasiveness and morbidity), without sacrificing fixation strength. Moreover, the present invention provides additional benefits including reduced destabilization and rotation of implants during deployment, mating, and final positioning.

Many of the contemporary medical devices for anchoring tendons and ligaments to bone provide some benefits only at a cost. The current gold standard for achieving superior fixation strength is to use interference screws but these require an open (non-arthroscopic) approach. For example, Arthrex' Bio-Tenodesis, and Tenodesis Screw systems can be difficult to use in an arthroscopic approach. Open approaches involve greater invasiveness, morbidity, and healing time as compared to endoscopic and arthroscopic techniques. The fixation strength of tenodesis interference screws averages about 234 N for ultimate pullout resistance. (See David P. Richards, M.D., F.R.C.S.C., and Stephen S. Burkhart, M.D., A Biomechanical Analysis of Two Biceps Tenodesis Fixation Techniques, *Arthroscopy: The Journal of Arthroscopic and Related Surgery*, Vol 21, No 7 (July), 2005: pp 861-866.)

Even excluding the drawback of an open approach typically required for using interference screws, they are not a perfect solution to the tenodesis repair problem. Using a tenodesis interference screw also requires an additional procedural step of whipstitching the tendon graft prior to using the fixation device. This step requires externalization of the tendon from the articular working space, a task disliked by many surgeons because it requires additional procedure time and can be difficult to perform. Additionally, most surgeons will find it necessary to remove surrounding cortical bone in order to fit both the device and the tendon into a tunnel or bore drilled into bone. This is an additional step that would preferably be omitted from the tenodesis procedure. If each procedure takes less time and difficulty, surgeons can perform more procedures per day and improve accuracy and efficiency.

Another disadvantage of relying on interference screws for tenodesis repair is that it can be difficult to recreate an anatomical fixation when using them. As the screw is rotated to seat it into the tunnel, the tendon often rotates along with the screw. The tendon can in that manner become wrapped around the screw and moved from its original placement. This undesirable process simultaneously alters the tension originally set by the surgeon in the muscle-tendon-bone complex and changes the intended mechanics of the fixation. A related difficulty of utilizing these devices lies in setting the initial graft tension. For example, in proximal biceps tenodesis, many surgeons report that it is difficult to set the proper tension to the biceps muscle if using a tenodesis interference screw for tendon fixation.

Current arthroscopic approaches generally provide significantly weaker fixation strengths, for example, ultimate pullout forces in the mid to low 100 N range. One of the simpler options currently available to perform an arthroscopic tenodesis repair is to use a suture anchor, such as the Depuy-Mitek G2 system. These devices require suturing the end of the tendon, placing an anchor into a decorticated bleeding bed at the desired fixation site, and then approximating the tendon to the attachment point by tensioning the sutures through the anchor and knotting them in place. Although this is a relatively easy procedure to complete arthroscopically, the fixation strength is limited by the holding force of the suture in the soft tissue of the tendon.

Accordingly, there is a need for a streamlined arthroscopic tenodesis repair procedure along with an integrated device for performing such procedure that avoids time-consuming preparations (whipstitching, externalization of the tendon) and provides greater fixation strengths comparable to those obtained through open techniques using interference screws. Additionally, there is a need to avoid the drawbacks of interference screws including especially, rotation of the tendon around the screw and deviation of the original tensions set by the surgeon caused by displacement of the muscle-tendon-bone complex and tendon graft.

BRIEF SUMMARY OF THE INVENTION

The present invention provides an integrated insertion and fixation device for tenodesis repair that is designed for an entirely arthroscopic approach. The device provides fixation strengths comparable to interference screws without the setbacks of interference screws.

More particularly, the present invention is a split barbed fixation device intended for soft tissue re-attachment of tendons and ligaments to bone. The system was developed to address a market need for a simple, strong intra-articular tenodesis repair compatible with a fully arthroscopic technique. The system is designed to minimize procedure time and steps, which may minimize limb distension while undergoing surgery and ultimately resulting in a better patient outcome. The word "tenodesis" used in the context of this application is defined as "the surgical anchoring of a tendon or ligament, as to a bone", so the term should be interpreted as having a broad application.

The system can be used with any suitably sized soft tissue tendon allograft or autograft, or native detached tendon where the surgical site location is accessible to the inserter, where there is sufficient volume at the intended attachment point in the bone to accommodate the anchor. Whip stitching the tendon is not required, as with many interference screw type fixation devices. Common orthopedic soft tissue tenodesis repairs include tendon re-attachment in the shoulder (proximal/distal biceps tenodesis) or ligament re-attachment in the knee (Medial Collateral Ligament and Lateral Collateral Ligament repair). During proximal biceps tenodesis, the long head of the biceps brachii tendon (LHBB) may be released from its attachment to the glenoid and re-attached to the humerus in the bicipital groove or humeral head using the disclosed tenodesis fixation device.

Tenodesis of the lateral collateral ligament (LCL) in the knee can be performed by using the device to attach the free ends of the soft tissue graft within tunnels drilled in both the fibula and the femur. Similarly, tenodesis of the medial collateral ligament (MCL) is performed by placing a graft and anchors in the medial tibia and femur.

In one embodiment, the integrated insertion and fixation device may comprise the following elements: a first implant; a second implant; a tendon grasper; a first implant retainer; and a depth limiting sheath. In one embodiment, the fixation device may further comprise one or more of the following, in any combination: a tendon grasping needle tube; an implant keyway; and a first implant retaining step.

The tendon grasper is integrated into the device to grasp a pierced tendon, thereby avoiding external whip stitching of the tendon.

The first implant and second implant mate with each other. Alternatively, these elements may be described as a first implant portion and second implant portion, collectively forming an implant upon mating.

In one embodiment, only one of the first and second implants or only one implant portion touches the tendon. This may be achieved, for example, by a distal end of one implant or implant portion extending further into the bone tunnel than the other implant or implant portion.

Various elements of the device secure the position of the implants to prevent dislodging and rotation during deployment and manipulation of either implant or of the tendon.

The depth limiting sheath comprises structure that contacts bone to signal when the first implant has been inserted sufficiently into a tunnel drilled into bone and to halt further insertion.

The first implant retainer comprises a notch to prevent the first implant from moving further into the tunnel drilled into bone when the second implant is deployed to mate with the first implant.

The tendon grasping needle tube houses the tendon grasper within it.

The implant keyway mates the first implant and the second implant to the tendon grasping needle tube, thereby preventing rotation of the implants during deployment and manipulation.

The first implant retaining step has a step structure that permits the first implant to be pounded into position in the tunnel drilled into bone by preventing the first implant from sliding up the tendon grasping needle tube.

With this device, the only preparation necessary is to drill a small diameter, shallow tunnel at the desired fixation site and to capture the free end of the graft tendon with the integrated tendon grasper.

In one embodiment, the implant may be comprised of an all polymer construction without any metal required.

In one embodiment, the insertion device for arthroscopic tenodesis repair, may comprise: a first implant; a second implant; a tendon grasper; a first implant retainer; and a depth limiting sheath. The depth limiting sheath may comprise structure that contacts bone to signal when the first implant has been inserted sufficiently into a tunnel drilled into bone and to halt further insertion. The first implant retainer may comprise a notch to prevent the first implant from moving further into said tunnel drilled into bone when the second implant is deployed to mate with the first implant.

In one embodiment, in addition to the elements disclosed in the previous paragraph, the insertion device may further comprise a tendon grasping needle tube and an implant keyway. The tendon grasping needle tube houses the tendon grasper within it and the implant keyway mates the first implant and the second implant to the tendon grasping needle tube, thereby preventing rotation of the implants during deployment and manipulation.

In one embodiment, in addition to the elements disclosed in the preceding two paragraphs, the insertion device may further comprise a first implant retaining step having a step structure that permits the first implant to be pounded into position in the tunnel drilled into bone by preventing the first implant from sliding up the tendon grasping needle tube.

In one embodiment, the present invention provides an implant for tenodesis repair that may comprise a first implant portion and a second implant portion. The second implant portion mates with the first implant portion. The first implant portion may comprise a plurality of softened barbs that face down into a tunnel drilled into a bone. In this manner, or according to alternative manners, the first implant may be structured to urge a tendon into surrounding bone. The second implant portion may comprise a plurality of barbs that face up towards an entrance to the tunnel. In this manner, or according to alternative manners, the second implant is structured to engage with surrounding bone.

In one embodiment of the implant for tenodesis repair only one implant portion contacts the tendon. In one embodiment, it is the first implant portion, introduced into the tunnel first, that contacts the tendon. In one embodiment of the implant after the second implant portion is mated with the first implant portion the distal end of the first implant portion extends deeper into the tunnel than the distal end of the second implant portion. In one embodiment, the first implant portion and the second implant portion may mate along an angle that is not parallel to an outer surface of either implant. In one embodiment of the implant, when the second implant portion is mated with the first implant portion, the distal end of the implant at a far end of the tunnel is wider than the proximal end of the implant at a near end of the tunnel. In this manner, or according to alternative manners, the wider distal end may be structured for positioning within cancellous bone. In this manner, or according to alternative manners, the narrower proximal end may be structured for positioning within cortical bone. This design of a non-uniform proximal and distal end, which may take the form of a wider distal end and a narrower proximal end, better distributes load across the implant and reduces a pinch point at an aperture at a proximal end of the tunnel.

In one broad aspect of the invention, a method for arthroscopic tenodesis repair is provided that comprises: drilling a small diameter, shallow tunnel at a desired fixation site; piercing a free end of a graft tendon with a needle point of an insertion device; capturing the free end of the graft tendon with an integrated tendon grasper; pounding a mallet knob to introduce the free end of the graft tendon and a first implant into the tunnel until a depth limiting sheath on the insertion device contacts bone; pounding the mallet knob again to mate a second implant with the first implant within the tunnel; releasing the free end of the graft tendon; and removing the insertion device from the tunnel.

In one embodiment of the method when the mallet knob is pounded initially to introduce the first implant within the drilled tunnel, the first implant does not slide up a tube from which it is deployed. In one embodiment of the method when the mallet knob is pounded again to mate the second implant with the first implant within the tunnel, the first implant is stable and does not move further into the tunnel. In one embodiment of the method when the mallet knob is pounded initially to introduce the first implant and then pounded again to mate the second implant with the first implant, rotation of the implants is prevented.

As noted above, it is within the spirit and scope of the invention to provide a device for tenodesis repair generally. The invention disclosed herein may also be used for other types of orthopedic soft tissue tenodesis repair, including ligament reattachment in the knee (Medial Collateral Ligament (MCL) and Lateral Collateral Ligament (LCL) repair). During MCL repair, the device disclosed herein can be used to place a graft and anchors in the medial tibia and femur. During LCL repair, the device disclosed herein can be used to attach free ends of a soft tissue graft within tunnels drilled into the fibula and the femur.

More particularly, there is disclosed a system for arthroscopic tenodesis repair, which comprises a first implant movable distally into a procedural site and a second implant mateable with the first implant and also movable distally into the procedural site. A tendon grasper is movable distally to extend through and capture a tendon to be re-attached to bone at the procedural site. A first implant retainer comprises a member extendable outwardly from the tendon grasper for engaging the first implant and retaining it in axial position relative to the tendon grasper while the second implant is moved distally.

The tendon grasper comprises a distal portion for piercing a tendon and a tendon grasping needle tube which is axially movable relative to the distal portion and houses the distal portion therein. The outwardly extendable member of the first implant retainer extends from and retracts into the tendon grasping needle tube. In preferred embodiments, the tendon grasping needle tube further comprises an implant keyway for mating the first implant and the second implant to said tendon grasping needle tube, thereby preventing rotation of the implants during deployment and manipulation. A notch, comprising a substantially flat surface, is provided on the first implant for engaging the outwardly extendable member of the first implant retainer.

The tendon grasper further comprises an outwardly movable member, or more preferably a plurality of such members or barbs, for securing the tendon to the tendon grasper.

The implant system further comprises a proximal handle portion, which comprises a mallet knob at a proximal end of the handle which is axially movable relative to the handle and a retaining pin which is removably placeable in the handle to prevent relative movement of the mallet knob and the handle. An actuator on the handle is provided for extending and retracting the outwardly movable member of the first implant retainer and the outwardly movable member on the tendon grasper.

A depth limiting sheath is also preferably provided, which comprises structure for contacting bone to prevent further distal deployment of the first implant into the procedural site.

In another aspect of the invention, there is provided an implant for tenodesis repair, which comprises a first implant portion and a second implant portion that is structurally separate from but mateable with the first implant portion. Each of the first and second implant portions comprise a diagonally oriented mating surface which is complementary to the mating surface of the other implant to form a mating line lying at an angle of between about 10 and 80 degrees from a longitudinal axis through the implant. When the first and second implant portions are in a mating orientation, the implant has a width which is substantially greater at a distal end thereof than at a proximal end thereof. In some embodiments, the angle is between about 30 and 60 degrees from the longitudinal axis through the implant, and in other embodiments, the angle is between about 40 and 50 degrees from the longitudinal axis through the implant.

The first implant further comprises a notch comprising a substantially flat surface for engaging with a first implant retainer, to hold the first implant in a fixed axial position while the second implant is moved axially to mate with the first implant. When the second implant portion is mated with the first implant portion, a distal end of the first implant portion extends deeper into the bone opening than a distal end of the second implant portion.

In still another aspect of the invention, there is disclosed a method for arthroscopic tenodesis repair, which comprises steps of creating an opening in bone at a desired fixation site, piercing a free end of a graft tendon with a distal end of an insertion device, capturing the free end of the graft tendon by outwardly extending a tendon grasper, actuating a mallet knob to move the insertion device distally, thereby introducing the free end of the graft tendon and a first implant disposed on the insertion device into the bone opening, actuating the mallet knob again to move a second implant distally until it mates with the first implant within the tunnel, releasing the free end of the graft tendon, and removing the insertion device from the tunnel. The method comprises a further step of extending a first implant retainer from the insertion device to engage the first implant, so that when the first mallet knob is actuated to introduce the first implant within the bone opening, the first implant does not move axially relative to the insertion device. The step of releasing the free end of the graft tendon also releases the first implant, so that when the insertion device removal step is performed, the tendon, first implant, and second implant remain in the bone opening. Importantly, only the first implant portion contacts the tendon. Preferably, the inventive method comprises a further step of removing a pin between the first mallet knob actuating step and the second mallet knob actuating step, wherein the removal of the pin permits the mallet knob to move axially relative to the insertion device when the mallet knob is actuated the second time. The mallet knob actuating steps are performed by pounding the mallet knob with a mallet.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 illustrates, in isolation, the first mating portion of the implant mated with the second mating portion of the implant, along a mating staggered step;

FIG. 4 is an isometric view showing additional elements at the distal end of the device through a cutaway view of the first implant, including a tendon grasping needle tube, first implant retaining step, and implant keyway;

FIG. 5 is an isometric view showing the distal end of the device, including the implant, tendon grasping needle tube, and tendon grasper, with the tendon grasper retracted within the tendon grasping needle tube;

DETAILED DESCRIPTION OF THE INVENTION

Figure 1:
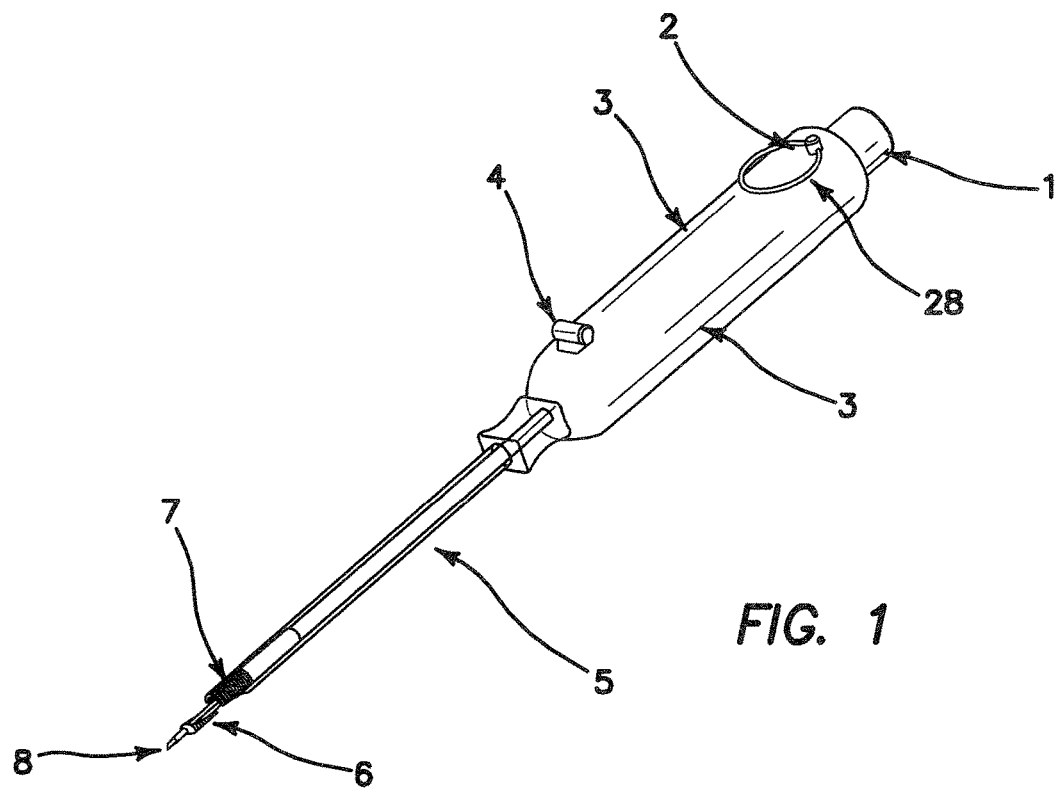
FIG. 1 is an isometric view showing most of the elements of an integrated insertion and fixation device constructed in accordance with the principles of the present invention, including the implant with two mating portions at the distal end and the handle and mallet knob at the proximal end.

The present invention comprises an integrated insertion and fixation device for tenodesis repair. The device comprises one or more of the following elements, in any combination: a first implant (or first implant portion); a second implant (or second implant portion); a tendon grasper; a first implant retainer; a depth limiting sheath; a tendon grasping needle tube; an implant keyway; and a first implant retaining step.

As used herein, the term first implant also refers to and is used interchangeably with first implant portion, and vice versa. Similarly, the term second implant also refers to and is used interchangeably with second implant portion, and vice versa.

In one embodiment, the invention comprises an implant comprising two mating portions or alternatively, a first implant 6 and a second implant 7 that are arranged to mate with one other (see FIGS. 3, 16, 17). The first implant or first implant portion 6 comprises a plurality of softened barbs that are arranged to face downwardly into a tunnel drilled into a bone when the implant is deployed, and is configured to urge a tendon into surrounding bone. The second implant or second implant portion 7 comprises a plurality of barbs that are arranged to face upwardly toward an entrance to the drilled tunnel when the implant is deployed, and is configured to engage with surrounding bone.

The first implant portion 6 and the second implant portion 7 are constructed to mate along engaged mating surfaces that lie along a mating line A that is disposed at an angle that is not parallel to a longitudinal axis B of either implant portion (see FIG. 3). In one embodiment, the first implant portion 6 and the second implant portion 7 mate along an oblique line formed by the engaged mating surfaces that is at an angle C of between ten and eighty degrees from a central axis extending through the first implant portion. More particularly, the angle C is between twenty and seventy degrees, and even more particularly the angle is between thirty and sixty degrees. In the illustrated embodiment, the angle C is between forty and fifty degrees.

When the second implant portion 7 is mated with the first implant portion 6, a distal end of the implant at a far end of the drilled bone tunnel or bore is wider than a proximal end of the implant at a near end of the drilled bone tunnel. This dimensional relationship can be seen, for example, in FIGS. 17a-17e. The wider distal end is structured to be positioned within cancellous bone. The narrower proximal end is structured to be positioned within cortical bone. This variation in width from the distal to proximal end of the implant serves to better distribute load across the implant and to reduce a pinch point at an aperture at a proximal end of the drilled tunnel.

In the disclosed embodiments, only one implant portion contacts the tendon. More particularly, only the first implant portion 6, which is inserted into the tunnel first, contacts the tendon.

In one broad aspect, the present invention provides a method for arthroscopic tenodesis repair, comprising: drilling a small diameter, shallow blind bore or tunnel at a desired fixation site; piercing a free end of a graft tendon with a needle point of an insertion device; capturing the free end of the graft tendon with an integrated tendon grasper 8; pounding a mallet knob to introduce the free end of the graft tendon and the first implant 6 into the drilled tunnel until a depth limiting sheath 5 on the insertion device contacts bone; pounding the mallet knob again to mate the second implant 7 with the first implant 6 within the drilled tunnel; releasing the free end of the graft tendon; and removing the insertion device from the drilled tunnel.

When a mallet knob 1 is pounded to mate the second implant 7 with the first implant 6 within the drilled tunnel, the first implant 6 is stable and does not move further into the drilled tunnel.

Moreover, when the mallet knob 1 is pounded initially to introduce the first implant 6 within the drilled tunnel, the first implant 6 does not slide upwardly along a tendon grasping needle tube 11 from which it is deployed.

Furthermore, when the mallet knob 1 is pounded initially to introduce the first implant 6 and again to mate the second implant 7 with the first implant 6, rotation of the implants is prevented.

The figures illustrate further various features of the present invention as described below.

Figure 2:
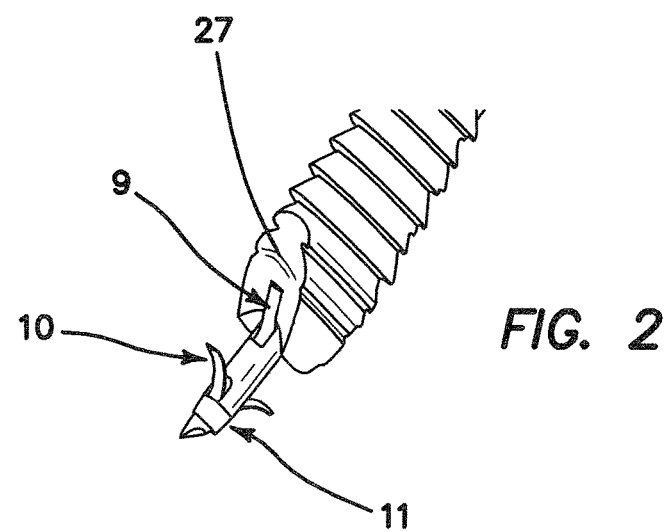
FIG. 2 is an isometric view showing the distal end of the device of FIG. 1, showing one mating portion of the implant, implant retainer, and tendon grasping needle tube with its barbs.

FIG. 1 shows many of the elements of the present invention including: the mallet knob 1, a pin 2, a handle 3, preferably constructed as two mateable handle halves, a tendon grasper lever 4, the depth limiting sheath 5, the first implant 6, the second implant 7, and the tendon grasper 8. FIG. 2 shows additional elements at the distal end of the device including a first implant retainer 9, tendon grasper barbs 10, and the tendon grasping needle tube 11. FIG. 3 shows first implant 6, introduced first, and second implant 7, introduced second, mating along a staggered step 14, which lies along the mating line A. FIG. 4 shows additional elements at the distal end of the device with a cutaway view through the first implant, including a first implant retaining step 15 and an implant keyway 16 for mating the implants to the tendon grasping needle tube 11 to prevent their rotation during manipulation by the user and deployment.

In operation, the mallet knob 1 is used to pound the first implant 6 and second implant 7 into place. The engagement pin 2 allows for the second implant 7 to be hammered into place after the first implant 6 is in position. The handle halves 3 collectively form the handle and can be readily disassembled to repair, replace, or realign parts. The tendon grasper lever 4 actuates the tendon grasper 8 with its tendon grasper barbs 10 and also actuates the implant retainer 9. The depth limiting sheath 5 prevents the first implant 6 from traveling further into the tunnel. The first implant 6 is introduced into the drilled tunnel first and is used to capture the tendon. The second implant 7 is introduced into the drilled tunnel second and is used to capture the bone. The tendon grasper barbs 10 of the tendon grasper 8 are used to grasp, manipulate, and retain a pierced tendon. The first implant retainer 9 is used to retain the first implant 6 as the second implant 7 is pounded into place. The tendon grasping needle tube 11 contains or houses the tendon grasper barbs 10 and tendon grasper 8 within it. The mating staggered step 14 is where the first implant 6 and the second implant 7 come together, lying along the diagonal mating line A relative to the central axis B and outer surfaces or sides of either implant. The first implant retaining step 15 allows the first implant 6 to be malleted into the bore or tunnel. The implant keyway 16 mates the first implant 6 and second implant 7 to the tendon grasping needle tube 11 and prevents rotation of the implants during deployment and manipulation by the user.

The system can be used with any suitably sized soft tissue tendon allograft or autograft or native detached tendon where the surgical site location is accessible to the inserter and there is sufficient volume at the intended attachment point in the bone to accommodate for the anchor. Whip stitching the tendon is not required as with many of the interference screw type fixation devices.

A procedure using the described system will now be described, noting that it is exemplary in nature, and may be varied to a certain extent depending upon the desired repair to be completed. As shown best, for example, in FIG. 15, a bore or tunnel 18 is drilled into a desired bone location, such as into the bone 20, which comprises an outer harder cortical layer 22 and inner softer cancellous bone 24. The illustrated bone is the humeral head (shoulder) of a patient, but could be any desired bone location suitable for the described techniques. In the illustrated procedure, the bore or tunnel 18 is a blind bore, extending only a portion of the way into the humeral head, but in some applications, the tunnel may be open at both ends, extending entirely through the bone structure.

Figure 6:
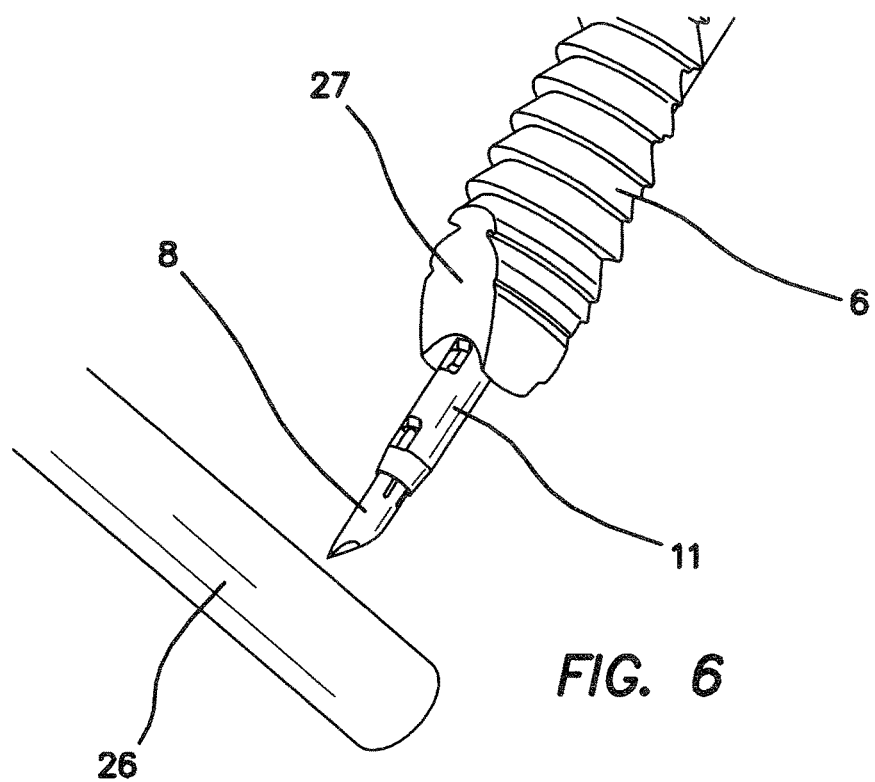
FIG. 6 is an isometric view showing the device with the tendon grasper in an exposed position just before tendon piercing.
Figure 7:
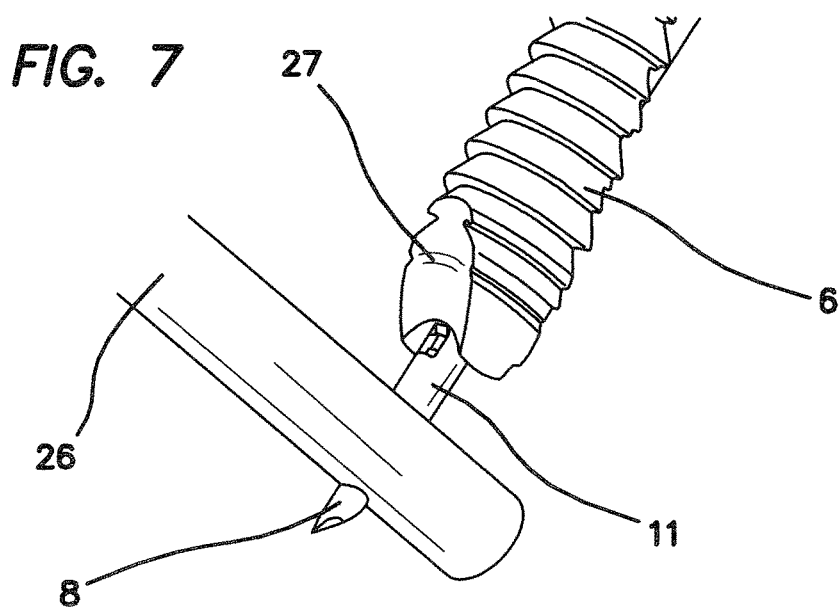
FIG. 7 is a view similar to FIG. 6, showing the device with the tendon grasper piercing the tendon.

Now referring particularly to FIGS. 6 and 7, a tendon 26 to be re-attached to the bone 20 is pierced by the sharp distal end of the tendon grasper 8, and the tendon grasper 8 is pushed distally entirely through the tendon 26 until it protrudes from its distal side.

Figure 8:
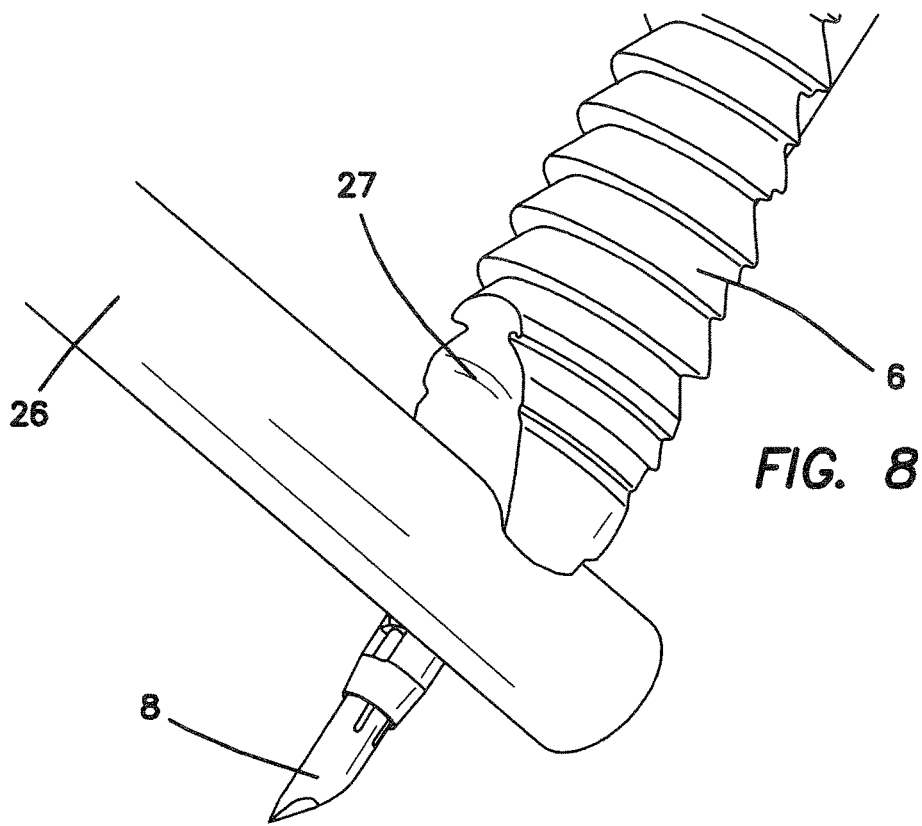
FIG. 8 is a view similar to FIGS. 6 and 7, showing the device with the tendon piercing completed and the first implant mating portion adjacent to the tendon.
Figure 9:
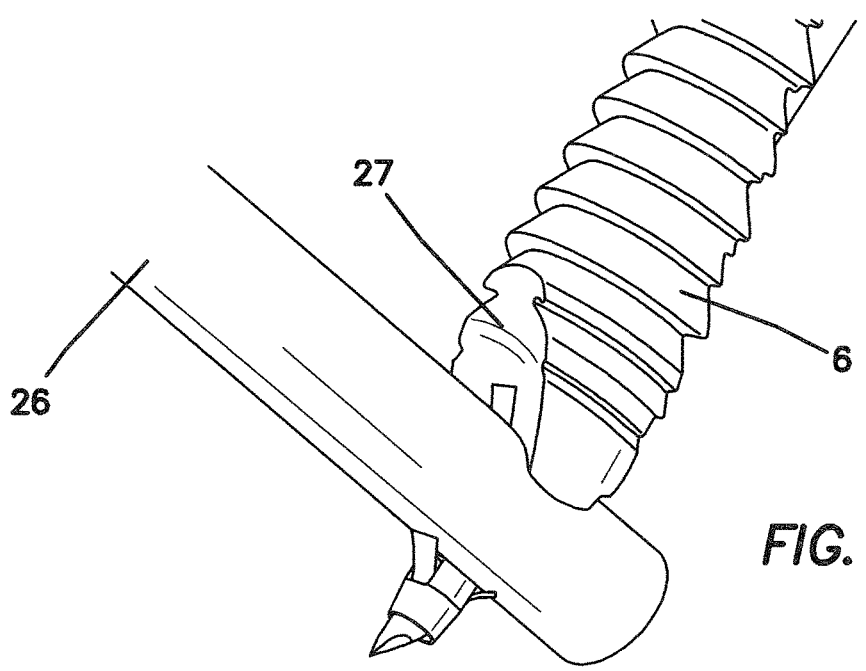
FIG. 9 is a view similar to FIGS. 6-8, showing the device with the tendon grasper barbs of the tendon grasper in an exposed and flexed or engaged position with the tendon.
Figure 10:
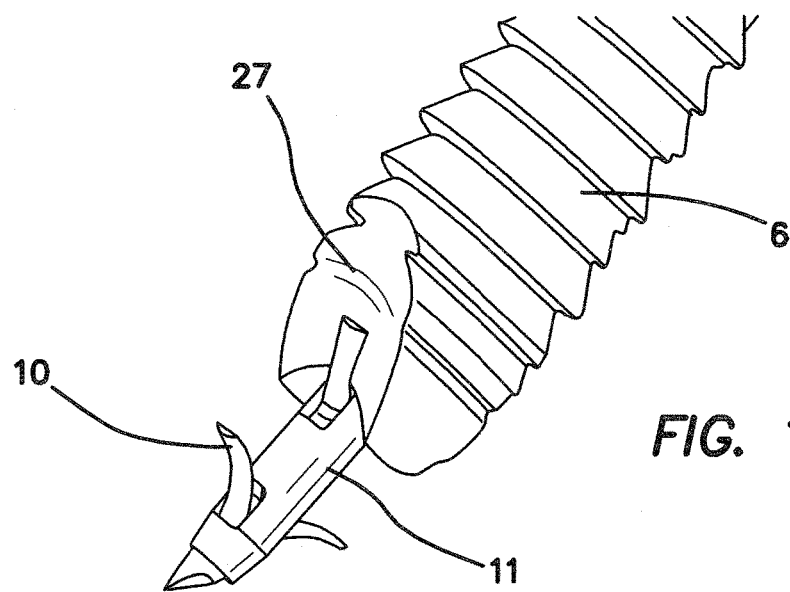
FIG. 10 is a view similar to FIGS. 6-9, showing the device with the tendon grasper barbs of the tendon grasper in an exposed and flexed or engaged position, without the tendon.
Figure 11:
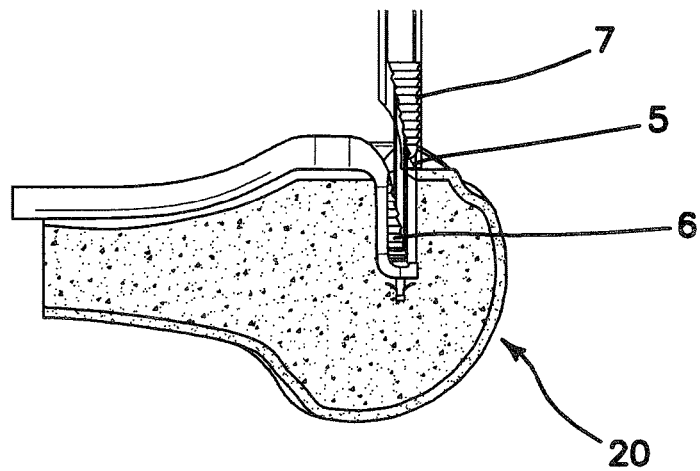
FIG. 11 shows the distal end of the device as the captured tendon and the first implant mating portion are pounded into a predrilled hole until the depth limiting sheath of the device contacts bone.
Figure 12:
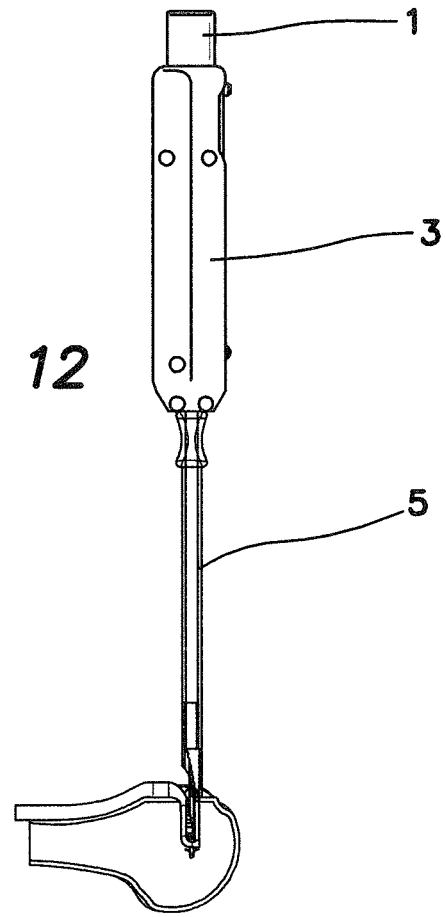
FIG. 12 shows the entire device as the captured tendon and the first implant mating portion are pounded into the predrilled hole until the depth limiting sheath of the device contacts bone, illustrating the handle and mallet knob at the proximal end of the device.
Figure 16A:
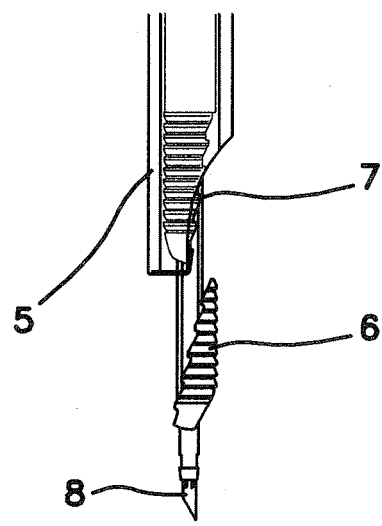
FIGS. 16A-16D illustrate a chronological progression of implant deployment with the second mating portion of the implant following the first mating portion of the implant.
Figure 16B:
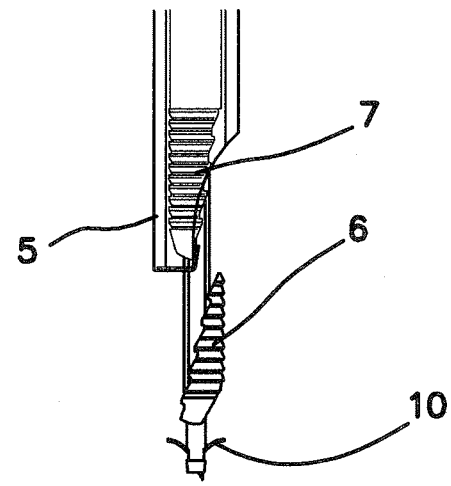

A mallet or other suitable instrument is now used to pound the mallet knob 1 (FIGS. 1, 12), which pushes the captured tendon 26 and the first implant 6 into the tunnel 18, as shown in FIGS. 11 and 12, until the depth limiting sheath 5 contacts the bone 20 to stop further distal movement of the first implant 6. FIG. 8 shows the relative positioning of the first implant 6 and the tendon 26 at the conclusion of this step. FIG. 16a shows the relative positioning of the first implant 6 and the second implant 7 after this step. The tendon grasper lever 4 is now slid into a proximal position to extend the tendon grasper barbs 10 outwardly, as shown in FIGS. 2, 4, 9, 10, and 16b, in order to secure the tendon 26 to the tendon grasper 8. This action also outwardly extends the first implant retainer 9 to secure the first implant 6 fixedly to the tendon grasping needle tube 11, as shown in FIGS. 2, 4, 9, and 10, so that the first implant 6 remains in axial position as the second implant 7 is moved distally. This is accomplished by engaging the implant retainer 9 with a flat surface or notch 27 on the first implant 6, as shown in Fig.

Figure 13:
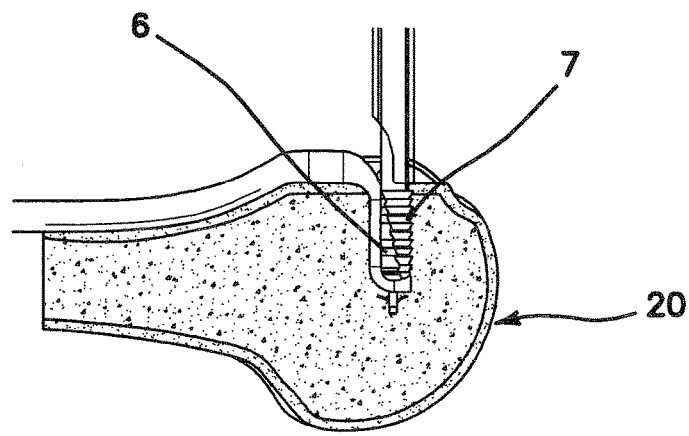
FIG. 13 shows the distal end of the device after the engagement pin at the proximal end of the device is removed so that the deployment knob can be pounded until it is flush with a proximal face of the handle in order to move the second implant mating portion into a mating relationship with the first implant mating portion.
Figure 14:
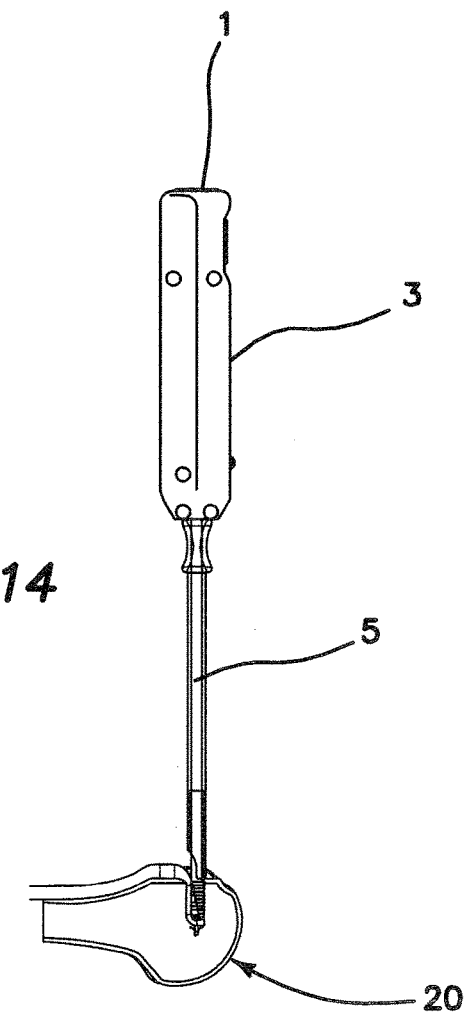
FIG. 14 shows the entire device after the engagement pin at the proximal end of the device is removed so that the deployment knob can be pounded until it is flush with a proximal face of the handle in order to move the second implant mating portion into a mating relationship with the first implant mating portion, illustrating the handle at the proximal end of the device with the mallet knob having been pounded flush with it and no longer protruding.
Figure 16C:
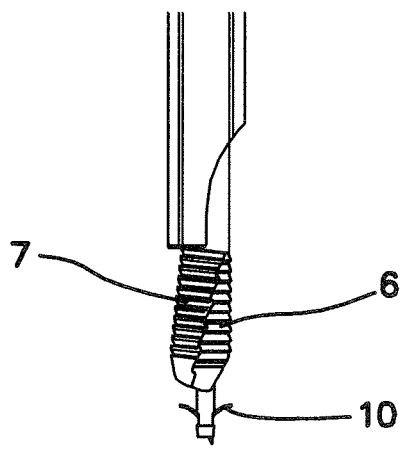
Figure 16D:
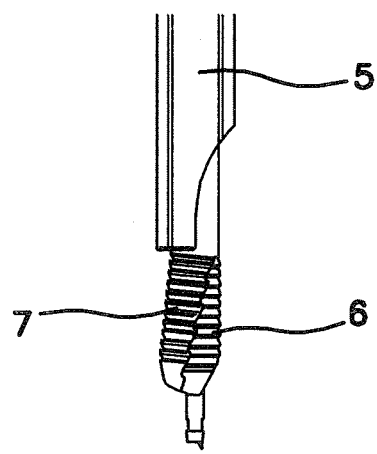
Figure 17A:
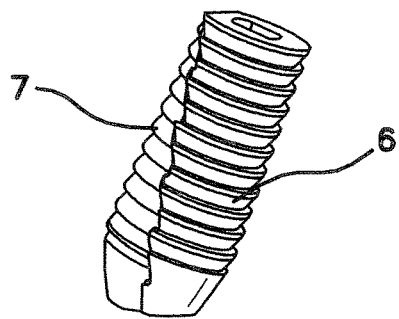
FIGS. 17A-17E show various perspectives of a deployed implant, wider at the base to accommodate softer cancellous bone and narrower at the top to accommodate harder cortical bone and to better distribute pressure, with the first implant mating portion mated with the second implant mating portion.
Figure 17B:
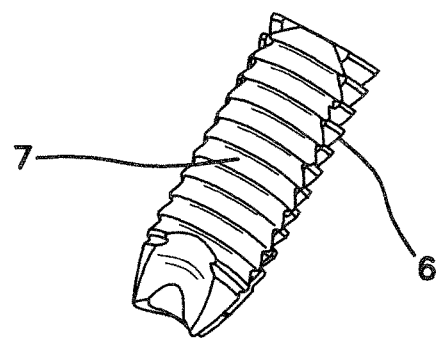
Figure 17C:
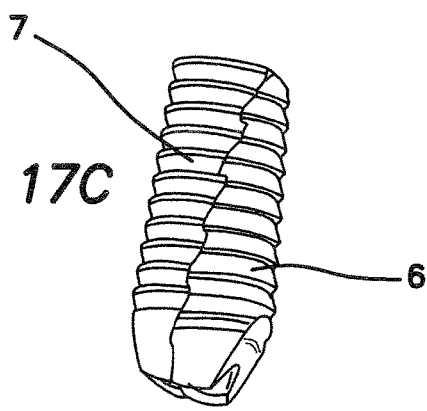
Figure 17D:
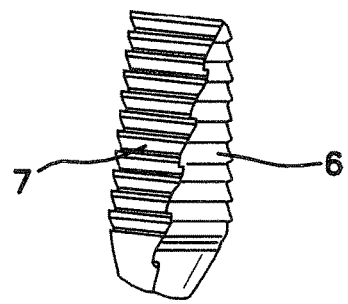
Figure 17E:
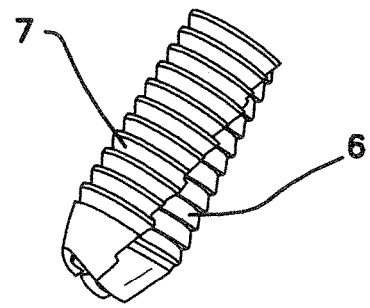

At this point, the pin 2 is pulled out of its keeper using an attached ring 28 (FIG. 1). The purpose of the pin 2 is to retain the mallet knob 1 in a fixed axial position relative to the handle 3, so that when the knob 1 is pounded with the pin in place, the entire structure moves distally to fix the first implant in position. Now, however, with the pin 2 removed, the mallet knob 1 is pounded again, and this time moves distally relative to the handle 3 until it is flush with the handle. This second pounding step, and relative movement of the mallet knob 1 to the handle 3, moves the second implant 7 distally a predetermined distance until it is mated with the first implant 6, as shown in FIGS. 13, 14, and 16c. The flush engagement of the knob 1 with the proximal end of the handle 3 functions as a stop to assist in the mating process.

Figure 15:
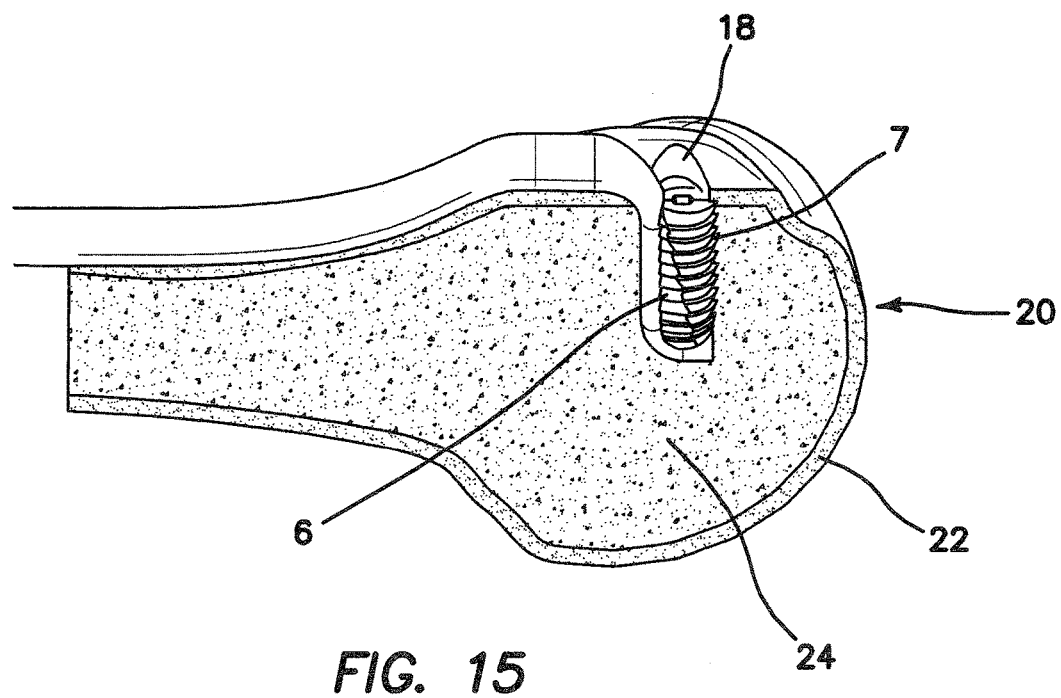
FIG. 15 shows a completed tenodesis repair using the device of the present invention with the first and second implant mating portions in place and the insertion device removed, and only the first implant mating portion is in contact with the tendon.

Once the foregoing step has been completed, the tendon grasping lever 4 is slid distally to retract the tendon grasper barbs 10 and the first implant retainer 9 back into the tendon grasping needle tube 11, as shown in FIGS. 5-8 and 16d. This functions to release the tendon 26 and the first implant 6 from the tendon grasping needle tube of the inserter, thus permitting the inserter to be withdrawn proximally out of the procedural site. FIG. 15 shows the completed repair, with the inserter removed.

FIGS. 17a-17e show the mated first and second implants 6 and 7, respectively, from various orientations, and particularly show the relative widths of the mated implants as being wider at the distal end and narrower at the proximal end.

The system and methods described herein permit a surgeon to perform a tenodesis repair using an all arthroscopic technique, requiring no complicated preparation of the tendon such as external whip stitching of the tendon, because it provides a solution for grasping the tendons integrated into the device. Thus, it offers a fixation strength comparable to a tenodesis interference screw, and eliminates the common problem of graft rotation associated with interference screw fixation. With this device, the only preparation necessary is to drill a small diameter, shallow tunnel or bore, at the desired fixation site and to capture the free end of the graft tendon with the integrated tendon grasper. The implant can be of an all-polymer construction, if desired, without any metal required.

The present invention is not limited to the embodiments described above. Various changes and modifications can, of course, be made, without departing from the scope and spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An implant for tenodesis repair, comprising:
   a first implant portion; and
   a second implant portion that is structurally separate from but mateable with said first implant portion, each of said first and second implant portions comprising a diagonally oriented mating surface which is complementary to the mating surface of the other implant to form a mating line lying at an angle of between about 10 and 80 degrees from a longitudinal axis through the implant;
   wherein when the first and second implant portions are in a mating orientation, the implant has a width which is greater at a distal end thereof than at a proximal end thereof.

2. The implant as recited in claim 1, wherein said angle is between about 30 and 60 degrees from the longitudinal axis through the implant.

3. The implant as recited in claim 2, wherein said angle is between about 40 and 50 degrees from the longitudinal axis through the implant.

4. The implant as recited in claim 1, wherein the first implant further comprises a notch comprising a substantially flat surface for engaging with a first implant retainer, to hold the first implant in a fixed axial position while the second implant is moved axially to mate with the first implant.

5. The implant as recited in claim 1, wherein when said second implant portion is mated with said first implant portion, a distal end of said first implant portion extends deeper into a bone tunnel than a distal end of said second implant portion.

6. The implant as recited in claim 1, wherein the first implant portion comprises a first plurality of barbs.

7. The implant as recited in claim 6, wherein the first plurality of barbs are arranged to face in a distal direction.

8. The implant as recited in claim 6, wherein the second implant portion comprises a second plurality of barbs.

9. The implant as recited in claim 8, wherein the second plurality of barbs are arranged to face in a proximal direction.

10. The implant as recited in claim 6, wherein the first plurality of barbs comprise softened barbs.

11. The implant as recited in claim 1, wherein the first and second implant portions are configured to mate along a staggered step which lies along the mating line.

12. The implant as recited in claim 1, wherein the first and second implant portions are formed from a polymer material.

13. The implant as recited in claim 1, wherein the first implant portion comprises a first implant retaining step configured to allow the first implant portion to be pounded into a bone tunnel by preventing the first implant portion from sliding relative to a tendon grasping device.

14. The implant as recited in claim 1, further comprising an implant keyway configured to mate the first and second implant portions to a tendon grasping device and prevent rotation of the first and second implant portions during deployment of the implant.

15. An implant for tenodesis repair, comprising:
   a first implant portion comprising a first plurality of barbs; and
   a second implant portion that is structurally separate from but mateable with said first implant portion, the second implant portion comprising a second plurality of barbs, each of said first and second implant portions comprising a diagonally oriented mating surface which is complementary to the mating surface of the other implant to form a mating line lying at an angle of between about 10 and 80 degrees from a longitudinal axis through the implant;
   wherein the first and second implant portions are formed from a polymer material; and
   wherein when the first and second implant portions are in a mating orientation, the implant has a width which is greater at a distal end thereof than at a proximal end thereof.

16. The implant as recited in claim 15, wherein the first plurality of barbs are arranged to face in a distal direction.

17. The implant as recited in claim 16, wherein the second plurality of barbs are arranged to face in a proximal direction.

* * * * *